United States Patent [19]

Baudin et al.

[11] Patent Number: 4,804,776

[45] Date of Patent: Feb. 14, 1989

[54] PROCESS FOR THE MANUFACTURE OF BENZENE DERIVATIVES

[75] Inventors: Josianne Baudin, Annemasse, France; Hans U. Gonzenbach, Geneva, Switzerland

[73] Assignee: Givaudan Corporation, Clifton, N.J.

[21] Appl. No.: 899,227

[22] PCT Filed: Nov. 27, 1985

[86] PCT No.: PCT/CH85/00168

§ 371 Date: Jul. 24, 1986

§ 102(e) Date: Jul. 24, 1986

[87] PCT Pub. No.: WO86/03486

PCT Pub. Date: Jun. 19, 1986

[30] Foreign Application Priority Data

Dec. 5, 1984 [CH] Switzerland ............... 05781/84
Nov. 13, 1985 [CH] Switzerland ............... 04866/85

[51] Int. Cl.$^4$ ............................................. C07C 69/76
[52] U.S. Cl. ................................. 560/51; 560/52; 560/60
[58] Field of Search ..................................... 560/53, 7

[56] References Cited

FOREIGN PATENT DOCUMENTS 180745 5/1986 European Pat. Off. ............. 69/71
2628469 12/1976 Fed. Rep. of Germany.
3320020 12/1983 Fed. Rep. of Germany.
657691 5/1929 France.

OTHER PUBLICATIONS

Lalande, R. et al., C. R. Acad. Sc. Paris, t, 258, (May 4, 1964), group 8, pp. 4567–4569.
"Compendium of Phase-Transfer Reactions and Related Synthetic Methods", Walter E. Keller, editor, 1st Edition, Fluka AG, Buchs, Switzerland (1979), p. 33.
"Organikum Organisch-Chemisches Grundpraktikum", Collective Authors, 6th Edition, VEB Deutscher Verlag Der Wissenschaften, Berlin, (1967), pp. 366–369, 376–381, 398–405.
F. Elsinger et al., Helv. Chim. Acta 43 (1960), 113–118.
P. Mueller et al., Tett. Letters 1973, 3565–3568.

Primary Examiner—Paul J. Killos
Attorney, Agent, or Firm—Robert F. Tavares; Linda A. Vag

[57] ABSTRACT

A novel process for the manufacture of p-tert.butylbenzene derivatives is described.

The process comprises reacting p-tert.butyl-benzyl chloride with a 2-formylpropionate of the formula

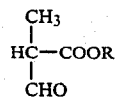

II wherein R represents lower-alkyl, e.g. $C_{1-6}$-alkyl, especially methyl or ethyl, and, if desired, converting the resulting compound of the formula

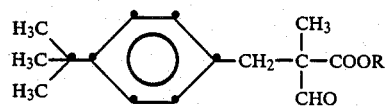

I wherein R has the above significance, optionally after purification, into p-tert.butyl-α-methyl-hydrocinnamaldehyde by decarbalkoxylation.

12 Claims, No Drawings

PROCESS FOR THE MANUFACTURE OF BENZENE DERIVATIVES

The present invention is concerned with a novel process for the manufacture of p-tert.butyl-benzene derivatives.

The products obtained according to the process in accordance with the invention are novel intermediates, which are suitable for the manufacture of a known odorant substance, or this odorant substance itself.

The process comprises reacting p-tert.butyl-benzyl chloride with a 2-formylpropionate of the formula

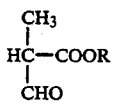

II wherein R represents lower-alkyl, e.g. $C_{1-6}$-alkyl, especially methyl or ethyl,
and, if desired, converting the resulting compound of the formula

I wherein R has the above significance,
optionally after purification, into p-tert.butyl-α-methyl-hydrocinnamaldehyde by decarbalkoxylation.

p-tert.Butyl-benzyl chloride is accessible in accordance with DT-OS (German Offenlegungsschrift) No. 3,320,020 in an economical in practically pure form. This halide can be oxidized according to Sommelet to give p-tert.butyl-benzaldehyde and the last-mentioned aldehyde can be condensed with propionaldehyde to give p-tert.butyl-α-methyl-cinnamaldehyde. By hydrogenation of the double bond in the side chain there is obtained the known odorant substance p-tert.butyl-α-methyl-hydrocinnamaldehyde (U.S. Pat. No. 2,875,131).

The present reaction sequence is more efficient as it avoids above all the Sommelet reaction, which owing to the accumulation of N-compounds such as methylamine and ammonia leads to an undesired pollution of the environment with harmful substances; in addition the energetically-unfavourable sequence oxidation/-(condensation)/reduction is avoided.

A further advantage lies in the fact that the reaction products of the individual steps are obtained in sufficient purity that they need not be purified prior to, where applicable, further reactions in accordance with the invention.

It would, indeed, have been simpler and more obvious from p-tert.butyl-benzyl chloride
(a) to proceed directly to p-tert.butyl-α-methyl-hydrocinnamaldehyde by alkylating propionaldehyde, or
(b) to proceed to p-tert.butyl-α-methyl-hydrocinnamaldehyde via the masked or modified form of p-tert.butyl-α-methyl-hydrocinnamaldehyde by alkylating a masked or modified propionaldehyde (e.g. an enamine, an imine etc), but unfortunately these two routes could not be realized.

Finally, it would also have been simpler to convert the compound I via the free acid directly into p-tert.butyl-α-methyl-hydrocinnamaldehyde, but this route could also not be realized.

The reaction of p-tert.butyl-benzyl chloride with the compound of formula II can be carried out under generally known alkylation conditions.

Thus, the reaction is conveniently carried out in a homogeneous phase, namely in an only slightly polar solvent, e.g. an aliphatic or aromatic hydrocarbon such as pentane, hexane, heptane, octane etc. or benzene, toluene etc. and in the presence of a non-nucleophilic base. Suitable bases are, in particular, metal hydrides such as alkali metal hydrides, e.g. lithium, sodium or potassium hydride, or tertiary alcoholates such as sodium tert.amylate or potassium tert.butylate etc. The presence of a quaternary ammonium compound as a catalyst is advisable, see e.g. Walter E. Keller, Compendium of Phase-Transfer Reactions and Related Synthetic Methods, 1st edition, Fluka AG, CH-9470 Buchs, Switzerland, 1979, 33.

The reaction temperature is not critical, the reaction can be carried out e.g. at room temperature or at an elevated temperature.

The formyl esters of formula I which are formed are novel compounds which are also an object of the present invention.

The optional further reaction of the formyl ester I is carried out in accordance with the invention by decarbalkoxylation, i.e. removal of the carboxylic acid ester group, while avoiding decarbonylation or deformylation.

This decarbalkoxylation of the compound I can be carried out e.g. by firstly converting the compound I into a compound of the formula

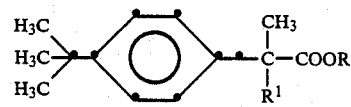

III wherein R has the above significance and $R^1$ represents a protected formyl group, e.g. an acetal (a dialkoxymethyl group), e.g. dimethyl acetal, diethyl acetal, or a cyclic derivative such as ethylene acetal (2,5-dioxa-cyclopentyl) etc.

The compound I is conveniently acetalized.

This acetalization can be carried out according to the known methods for the acidic reaction of aldehydes with mono- or divalent alcohols or with orthoformic acid alkyl esters in a medium which is as anhydrous as possible, see e.g. Organikum, Organisch-Chemisches Grundpraktikum, collective authors, 6th edition, VEB, Deutscher Verlag der Wissenschaften, Berlin, 1967, 376 et seq.

Thereupon, the ester group of III is suponified in a manner known per se by usual base and heat treatment, as is conventional for carboxylic acid esters (Organikum, loc. cit.,367, 399 et seq).

There thus result the acids of the formula

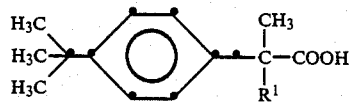

IV wherein $R^1$ represents a protected formyl group, e.g. an acetal (a dialkoxymethyl group), e.g. dimethyl acetal, diethyl acetal, or a cyclic derivative such as ethylene acetal (2,5-dioxa-cyclopentyl) etc.

These acids are novel and form a further object of the present invention.

Their conversion into p-tert.butyl-α-methyl-hydrocinnamaldehyde can finally be carried out by an acidic, known per se cleavage of the protecting group of IV under the influence of heat (e.g. at reflux temperatures). In this cleavage of the protecting group decarboxylation takes place at the same time, as the intermediately-formed α-formyl-carboxylic acid

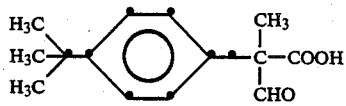

has a low stability (Organikum, loc. cit. 377).

This cleavage is conveniently carried out in a solvent, e.g. an aliphatic ketone such as acetone, methyl ethyl ketone, diethyl ketone etc.

According to a further process variant the decarbalkoxylation of I is initiated by means of a nucleophilic agent.

The nucleophilic agent serves to dealkylate the carboxylic acid alkyl ester, namely to convert the ester I into the anion of the acid IV'.

NaI or LiI is preferably used for this purpose (see F. Elsinger, J. Schreiber, A. Eschenmoser, Helv. Chim. Acta 43, (1960), 113 et seq and P. Muller, B. Siegfried, Tetrahedron Letters, (1973), 3565 et seq). In the case of LiI the anhydrous or water of crystallization-containing material can be used. However, other alkyl iodides as well as other alkyl halides such as the chlorides or bromides, or pseudo halides, e.g. rhodanides, also come in to consideration.

The amount of salt which is used is at least stoichiometric, but of course an excess is also possible. An excess which is higher than, for example, about 10-20% is, however, uneconomical.

In an especially preferred embodiment this process variant is carried out in a high-boiling polar solvent, e.g. hexamethylphosphoric acid triamide (HMPT). In this case, the compound III is conveniently added dropwise to a hot (e.g. 200°-250° C.) solution of the nucleophile in HMPT. The heat treatment leads simultaneously to a decarboxylation.

A polyether e.g. polyethylene oxide, polypropylene oxide, diglyme etc, can, however, also be used in place of HMPT.

EXAMPLE 1

(a) A reaction vessel, which is equipped with a stirrer, a thermometer and a dropping funnel, is flushed with nitrogen and then 1.9 g of sodium hydride (55% dispersion in mineral oil, 43 mmol) freed from oil with hexane and 50 ml of dry toluene are added; the suspension is heated to 60° C. 5 g (43.1 mmol) of freshly distilled methyl α-formylpropionate in 25 ml of dry toluene are added within 5 minutes. After one hour the mixture is cooled to room temperature and 1.5 g (3 mmol) of methyl-trioctylammonium iodide are added thereto. The methyl-trioctylammonium iodide was previously dried azeotropically with toluene. Thereupon, 7.9 g (43.1 mmol) of p-tert.butyl-benzyl chloride in 25 ml of dry toluene are added rapidly thereto. The mixture is stirred for 8 hours, left to stand for 12 hours and again stirred for 4 hours at 45° C. A gas-chromatographical analysis shows that the reaction has finished after this time. Water is cautiously added at room temperature and the mixture is extracted with ether. The organic phase is washed with water, 2N sulphuric acid, 10% sodium bicarbonate solution and saturated sodium chloride solution, dried over magnesium sulphate and concentrated. There result 13.9 g of crude oil which still contains 2.6 g of toluene. According to gas-chromatographical analysis the residue consists to 86% of methyl 2-formyl-2-p-tert.butyl-benzyl-propionate. The yield amounts to 86%. A sample is distilled and shows the following data:

NMR (60 MHz, CDCl$_3$) [ppm (δ)]: 1.33 singlet broad 12H, 3.15 doublet J=2 Hz 2H, 3.75 singlet sharp 3H, 7-7.5 multiplet 4H, 9.9 singlet sharp 1H.

(a bis) In an analogous manner, by alkylating ethyl α-formylpropionate there is obtained ethyl 2-formyl-2-p-tert.butyl-benzyl-propionate.

NMR (60 MHz, CDCl$_3$) [ppm(δ)]: 1.32 singlet projecting from the signal complex of a total of 15H, 3.15 doublet J=2 Hz 2H, 4.22 quartet J=7 Hz 2H, 7-7.5 multiplet 4H, 9.9 singlet sharp 1H.

(b) 9.8 g of the above formyl ester (containing 26 mmol of active substance) are dissolved in 50 ml of methanol and 1 ml of acetyl chloride are added. The mixture is stirred at room temperature for 15 minutes and thereupon heated to 60° C. for 5 hours. The mixture is cooled, water is added thereto, the mixture is neutralized with sodium bicarbonate, extracted with ether (previous washing with saturated sodium chloride solution) and the organic phase is dried over magnesium sulphate. After evaporation of the solvent there remain behind 9 g of a crude oil which contains according to gas-chromatographical analysis 5% of methyl 2-formyl-2-p-tert.butyl-benzyl-propionate and 74% of methyl 2-[formyl-dimethylacetyl]-2-[p-tert.butyl-benzyl]-propionate; the yield accordingly amounts to 22 mmol (85%). A sample is distilled and shows the following data:

B.p. 146° C./0.6 mmHg; $n_D^{25}$=1.4925.

(b bis) Ethyl 2-formyl-2-p-tert.butyl-benzyl-propionate is acetalized in the same manner to give ethyl 2-[formyl-dimethylacetal]-2-[p-tert.butyl-benzyl]-propionate.

B.p. 115° C./0.1 mmHg; $n_D^{20}$=1.4894

(b ter) Analogous treatment of ethyl 2-formyl-2-p-tert.butyl-benzyl-propionate in ethanol in place of methanol yields ethyl 2-[formyl-diethylacetal]-2-[p-tert.butyl-benzyl]-propionate.

B.p. 150° C./0.07 mmHg; $n_D^{20}$=1.4809

(b quater) Heating of ethyl 2-formyl-2-p-tert.butyl-benzyl-propionate at reflux temperature for 3 hours in a mixture of ethylene glycol and toluene (5:1) with the addition of 1% of p-toluenesulphonic acid yields ethyl 2-[formyl-ethyleneacetal]-2-[p-tert.butyl-benzyl]-propionate.

B.p. 150° C./0.4 mmHg; $n_D^{20}$=1.5010.

(c) 9.2 g of sodium hydroxide in 13.8 g of water are added to 7.5 g of the crude material from (b) (18 mmol of dimethyl acetal) in 25 ml of methanol. The mixture is held under reflux temperature for 1 hour, cooled, diluted with water and extracted with ether. 1.8 g of a neutral material remain behind after evaporation of the solvent. The aqueous phases are brought to pH 4 by means of 2N sulphuric acid and extracted with ether. The organic extract is washed with saturated sodium chloride solution, dried over magnesium sulphate and, after evaporation of the solvent, gives 2-[formyl-dimethylacetyl]-2-[p-tert.butyl-benzyl]-propionic acid in 99% purity; melting point 116°–118° C.; yield 92%.

(c bis) The analogous treatment of ethyl 2-[formyl-dimethylacetal]-2-[p-tert.butyl-benzyl]-propionate leads to the same product.

(c ter) Correspondingly, ethyl 2-[formyl-diethylacetal]-2-[p-tert.butyl-benzyl]-propionate is saponified in ethanol to give 2-[formyl-diethylacetal]-2-[p-tert.butyl-benzyl]-propionic acid.

M.p. 144°–145° C.

(c quater) Analogously, from ethyl 2-[formyl-ethyleneacetal]-2-[p-tert.butyl-benzyl]-propionate there is obtained 2-[formyl-ethyleneacetal]-2-[p-tert.butyl-benzyl]-propionic acid.

M.p. 99°–101° C.

(d) Under a nitrogen atmosphere 4.45 g of the crude acid of Example (1c) or (c bis) in a mixture of 50 ml of methyl ethyl ketone and 50 ml of 2N sulphuric acid are heated to reflux temperature and held at this temperature for 40 minutes. The mixture is thereupon cooled, water is added thereto, the mixture is extracted with diethyl ether, the organic phases are washed with saturated sodium chloride solution and dried over magnesium sulphate. After evaporation of the solvent there are obtained 3.3 g of practically pure p-tert.butyl-α-methyl-hydrocinnamaldehyde; yield quantative. After bulb-tube distillation 2.8 g of the aldehyde give 2.4 g of aldehyde in a purity of >99%.

(d bis) In an analogous manner, 2-[formyl-diethylacetal]-2-[p-tert.butyl-benzyl]-propionic acid and 2-[formyl-ethyleneacetal]-2-[p-tert.butyl-benzyl]-propionic are converted into p-tert.butyl-α-methyl-hydrocinnamaldehyde, whereby in the latter case acetone is used as the solvent in place of methyl ethyl ketone.

EXAMPLE 2

(a) 5 ml of hexamethylphosphortriamide (HMPT) and 1 g of LiI.H₂O are heated to 240° C. under a nitrogen atmosphere. 1.1 g of crude methyl 2-formyl-2-p-tert.butyl-benzyl-propionate (82%) in 1 ml of HMPT are added thereto, the mixture is stirred for 1 minute, poured on to ice and extracted with hexane. After washing with 2N HCl, with sodium bicarbonate solution and water the organic phase is dried over magnesium sulphate and the solvent is evaporated. 0.9 g of crude p-tert.butyl-α-methyl-hydrocinnamaldehyde is obtained. After bulb-tube distillation 500 mg of this aldehyde give 300 mg of pure material. The yield therefore amounts to 78.8%.

(b) When 1 g of NaI is used in the above Example in place of LiI.H₂O, an analogous result is obtained.

The gas-chromatographical analysis referred to in the above Examples are carried out using the column packings: 2% Apiezon L on Chromosorb G (AW/DMCS 80/100) [acid-washed/treated with dimethyldichlorosilane].

We claim:
1. A compound of the formula

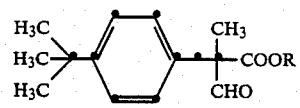

I wherein R represents a lower-alkyl group of one to six carbon atoms.

2. A compound in accordance with claim 1 which is Methyl 2-formyl-2-p-tert.butyl-benzyl-propionate.

3. A compound in accordance with claim 1 which is Ethyl 2-formyl-2-p-tert.butyl-benzyl-propionate.

4. A compound of the formula

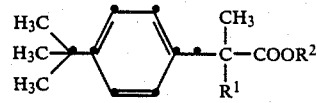

III' wherein:
$R^1$ represents a protected formyl group and
$R^2$ represents hydrogen or a lower-alkyl group of one to six carbon atoms.

5. A compound in accordance with claim 4, wherein the formyl group is acetalized.

6. A compound in accordance with claim 4 which is Methyl 2-(formyl-dimethylacetal)-2-(p-tert.butyl-benzyl)-propionate.

7. A compound in accordance with claim 4 which is Ethyl 2-(formyl-dimethylacetal)-2-(p-tert.butyl-benzyl)-propionate.

8. A compound in accordance with claim 4 which is Ethyl 2-(formyl-diethylacetal)-2-(p-tert.butyl-benzyl)-propionate.

9. A compound in accordance with claim 4 which is Ethyl 2-(formyl-ethyleneacetal)-2-(p-tert.butyl-benzyl)-propionate.

10. A compound in accordance with claim 5 which is 2-(Formyl-dimethylacetal)-2-(p-tert.butyl-benzyl)-propionic acid.

11. A compound in accordance with claim 5 which is 2-(Formyl-diethylacetal)-2-(p-tert.butyl-benzyl)-propionic acid.

12. A compound in accordance with claim 5 which is 2-(Formyl-ethyleneacetal)-2-(p-tert.butyl-benzyl)-propionic acid.

* * * * *